(12) United States Patent
Flesselles et al.

(10) Patent No.: US 6,503,514 B1
(45) Date of Patent: Jan. 7, 2003

(54) ATTENUATED STRAINS OF MYCOBACTERIA

(75) Inventors: Bruno Flesselles, Toronto (CA); Michel H. Klein, Willowdale (CA)

(73) Assignee: Aventis Pasteur Limited, Toronto (CA)

( * ) Notice: Subject to any disclaimer, the term of this patent is extended or adjusted under 35 U.S.C. 154(b) by 0 days.

(21) Appl. No.: 09/612,481

(22) Filed: Jul. 7, 2000

Related U.S. Application Data

(62) Division of application No. 08/915,709, filed on Aug. 21, 1997, now Pat. No. 6,136,324.
(51) Int. Cl.[7] .......................... A61K 39/04; C12N 1/00; C07K 1/00; C07H 21/04
(52) U.S. Cl. ................ 424/248.1; 424/93.2; 424/200.1; 424/243; 435/243; 435/253.1; 435/441; 435/471; 530/300; 530/350; 530/800; 530/825; 536/23.1; 536/23.7
(58) Field of Search .............................. 424/93.2, 200.1, 424/243, 248.1; 435/243, 253.1, 441, 471; 530/300, 350, 820, 825; 536/23.1, 23.7

(56) References Cited

U.S. PATENT DOCUMENTS

| 4,681,762 A | 7/1987 | Oeschger et al. .............. 424/92 |
| 5,663,317 A | 9/1997 | Falkow et al. .............. 536/23.7 |
| 5,700,683 A | 12/1997 | Stover et al. .......... 435/252.31 |

FOREIGN PATENT DOCUMENTS

| WO | WO 95/06726 | 3/1995 |
| WO | WO 95/17511 | 6/1995 |
| WO | WO 98/01559 | 1/1998 |

OTHER PUBLICATIONS

Parker, S.L., et al "Comparison of PCR–generated fragments of the mce gene from *Mycobacterium tuberculosis*, M. avium, M. intracelluare, and M. scrofulaceum" Clinical and Diagnostic Laboratory Immunology, vol. 2, No. 6, pp. 770–775. Nov. 1995.*

Grange, J.M.; Gibson J; Osborn, T.W.; Collins, C.H. and Yates, M.D. (1983), Tubercle 64: 129–139.

Shepard, C.C. (1958), J. Exp. Med. 107: 237–45.

Arruda, S., Bonfim, G.; Huma–Byron, T. and Riley L.W. (1993), Science 261: 1454–1457.

Azad, A.K., Sirakova T.D., Rogers L.M., Kolttukudy P.E. (1996) PNAS 93: 4787–4792.

Balasubramanicm V.M. et al (1996) J. Bacteriol 178:273–279.

Reyrat J.M., Berthet F.X., Gicquel B. (1995) PNAS 92:8768–8772.

Reyrat JM, Lopez–Ramirez G, Ofredo C, Gicquel B, Winter N. (1996), Urease activity does not contribute dramatically to persistence of Mycobacterium bovis bacillus Calmette–Guerin. Infect. Immun. 64. pp 3934–3936.

Jacobs Jr WR., Kalpana GV., Cirillo JD., Pascopella L, Snapper SB., Udani RA., Jones W., Barletta RG., Bloom BR. (1991) Genetic systems for Mycobacteria. Methods Enzymol. 204 pp 537–555.

Anderberg, R.J., Strachan, J.A. and Cangelosis, G.A. (1995) Bio Techniques 18:217–219.

Parker et al, "Comparison of PCR–generated fragements of the mce gene from *Mycobacterium tuberculosis*, M, avium, M. intracellulare, and M scrofulaceum" Clin, Diag. Lab. Immunol., vol. 2, No. 6, pp. 770–775.

* cited by examiner

Primary Examiner—Rodney P Swartz
(74) Attorney, Agent, or Firm—Sim & McBurney (57) ABSTRACT

Attenuated strains of Mycobacterium, particularly species of the tuberculosis complex, have the mycobacterial cell entry (mce) gene functionally disabled. The gene may be disabled by an insertion into the gene which disrupts the mycobacterial cell entry function thereof of a selectable marker which is used for screen for homologous recombinants in which a double cross-over event has been effected. The attenuated strains may be used in the immunization of hosts against Mycobacterium disease.

4 Claims, 4 Drawing Sheets

Figure 1: Construction and map of the disrupted *mce* gene

Figure 2: Screening of hygromycin-resistant BCG colonies by PCR to detect double cross-over events.

Figure 3: Southern Blot of Chromosomal DNA from some hygromycin resistant BCG

Lane 1 : BCG wt SacI
Lane 2 : BCG-65 SacI
Lane 3 : BCG-69 Sac I
Lane 4 : BCG wt XhoI Lane 5 : BCG-65 XhoI
Lane 6 : BCG-69 XhoI
Lane 7 : BCG-73 XhoI
Lane 8 : BCG-83 XhoI

FIGURE 4

Western Blot of hygromycin resistant

Lane 1 : BCG-65
Lane 2 : BCG-69
Lane 3 : BCG wild type

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
      (A) LENGTH: 21 base pairs
      (B) TYPE: nucleic acid
      (C) STRANDEDNESS: single
      (D) TOPOLOGY: linear    (xi) SEQUENCE DESCRIPTION: SEQ ID NO: 1:

GTATGTGTCG TTGACCACGC C      21

(2) INFORMATION FOR SEQ ID NO: 2:

(i) SEQUENCE CHARACTERISTICS:
      (A) LENGTH: 24 base pairs
      (B) TYPE: nucleic acid
      (C) STRANDEDNESS: single
      (D) TOPOLOGY: linear    (xi) SEQUENCE DESCRIPTION: SEQ ID NO: 2:

TCAGGTCGAT CGGCATCGTA GAAG      24

(2) INFORMATION FOR SEQ ID NO: 3:

(i) SEQUENCE CHARACTERISTICS:
      (A) LENGTH: 21 base pairs
      (B) TYPE: nucleic acid
      (C) STRANDEDNESS: single
      (D) TOPOLOGY: linear    (xi) SEQUENCE DESCRIPTION: SEQ ID NO: 3:

TTTCAAACGT TCCTGCGTCC C      21

(2) INFORMATION FOR SEQ ID NO: 4:

(i) SEQUENCE CHARACTERISTICS:

```
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 4:

CGAGTTTGAC GATTCCAG                                                    18
```

ATTENUATED STRAINS OF MYCOBACTERIA

REFERENCE TO RELATED APPLICATION

This patent application is a division of U.S. Pat. application Ser. No. 08/915,709 filed Aug. 21, 1997 (now U.S. Pat. No. 6,136,324).

FIELD OF INVENTION

The present invention relates to the field of molecular immunology and, in particular, to attenuated strains of Mycobacterium and immunogenic preparations comprising the same.

BACKGROUND TO THE INVENTION

Tuberculosis (TB) is a major cause of mortality throughout the world, particularly in developing countries. There are about 8 to 9 million new cases of clinical disease reported every year and the number of deaths is estimated to be about 3 million. In the U.S. the trend of steady decline in TB has reversed and the problem is compounded by increasing numbers of drug-resistant strains. The tuberculosis complex is a group of four mycobacterial species that are genetically closely related. The three most important members are *Mycobacterium tuberculosis*, the major cause of human TB; *Mycobacterium africanum*, a major human pathogen in some populations; and *Mycobacterium bovis*, the cause of bovine TB. None of these mycobacteria is restricted in being pathogenic for a single-host species.

In addition to being an important human disease, TB is also a major veterinary problem in many countries. Infection of cattle with *M. bovis* results in bovine TB and all animals showing any signs of infection are systematically slaughtered. The economic losses are thus extensive, and furthermore, cattle can serve as a reservoir for human disease.

In a majority of cases of infection, inhaled tubercle bacilli are ingested by phagocytic alveolar macrophages and are either killed or grow intracellularly to a limited extent in local lesions called tubercules. In this way the infection is limited and the primary sites of infection are walled off without any symptoms of disease being observed. Such individuals have a lifetime risk of about 10% for developing active disease. In a latter eventuality, bacilli spread from the site of infection in the lung, through the lung and via lymphatics or blood to other parts of the body producing characteristic solid caseous (cheese-like) necrosis in which bacilli survive. If the necrotic reaction expands breaking into a bronchus, or in the worst case, if the solid necrosis liquefy, a rapid proliferation of the bacilli occurs. The pathological and inflammatory processes set in motion then produce the characteristic weakness, fever, chest pain, cough and bloody sputum which are the hallmarks of active TB.

Effective treatment of TB with antibiotics exists. However, this is expensive and requires prolonged administration of a combination of drugs. There is a problem in compliance with the drug administration regime because of the extended time periods involved and this has contributed to the appearance of drug-resistant strains. There is a recognized vaccine for TB which is an attenuated form of *M. bovis*, known as BCG (bacille Calmette Guérin). This strain was developed in 1921 and the basis for its attenuation is still not known (ref. 1—throughout this application, various references are cited in parentheses to describe more fully the state of the art to which this invention pertains. Full bibliographic information for each citation is found at the end of the specification, immediately preceding the claims. The disclosure of these references are hereby incorporated by reference into the present disclosure). The efficacy of BCG as a TB vaccine is a subject of controversy and has been estimated in various trials to be anywhere between 0 and 70%.

The molecular basis for the virulence and pathogenesis of *M. tuberculosis* has not been extensively described. Some virulence factors, particularly those related to the sigma factors have been recently identified (ref. 2). *M. tuberculosis* can enter non-phagocytic cells in culture, such as HeLa cells (ref. 3) and once inside can multiply and survive. Recently, a protein encoded by a DNA fragment (1535 bp long) from a strain of *M. tuberculosis* (H37Ra) was reported to mediate the entry of the bacterium and its survival in mammalian cells (ref. 4). This DNA fragment when introduced into a non-pathogenic strain of *E. coli* is able to confer invasiveness to the bacterium, and survival for up to 24 hours in human macrophages. The mce (mycobacterial cell entry) gene was mapped to an Open Reading Frame (ORF) extending from position 182 to 810 on the 1535 bp DNA fragment mentioned above and encodes a protein of molecular weight between 22 and 27 kDa. Subsequent work has shown the gene described in ref. 4 is not a full length gene.

In copending U.S. patent application Ser. No. 08/677,970 filed Jul. 10, 1996, assigned to the assignee hereof and the disclosure of which is incorporated herein by reference, there is described the isolation and characterization of genes encoding proteins of mycobacteria associated with cell binding and cell entry and the protein encoded thereby. This gene is referred to herein as the Mycobacterial cell entry (mce) gene and the encoded protein the Mycobacterial cell entry protein (Mcep).

As described therein, restriction enzymes digestion of *M. bovis* BCG DNA and subsequent Southern blot analysis using a PCR amplified product as a probe, indicated the presence of the mce gene on 1.5 kb and 5 kb fragments of Sal I and Xho I digests. The corresponding bands were cut from the Southern blots and ligated into suitably digested pUC18 and pBluescript II (sk+) plasmids respectively. The libraries obtained after transformation of competent *E. coli* libraries were probed for the mce gene by hybridization and two positive clones were identified. The clones were grown, plasmids isolated and analyzed to yield two plasmids: pBCGcepX containing an approximately 5 kb DNA insert hybridizing to mce gene-specific probe and another plasmid pBCGcepS containing a 1.5 kb Sal I insert also hybridizing to the mce-specific probe.

The inserts of plasmids pBCGcepX and pBCGcepS were sequenced by the primer walking technique. The sequence data from the inserts was aligned and it was found that the 1.5 kb Sal I insert of plasmid pBCGcepS was an internal fragment of the larger pBCGcepX clone. The complete sequence of the 4740 bp DNA fragment clones into pBCGcepX is shown in FIG. 4 of application Ser. No. 08/677,970. Plasmid pBCGcepX has been deposited with ATCC under deposit number 97511 on Apr. 11, 1996.

Mycobacterial infection may lead to serious disease. It would be advantageous to provide attenuated strains of Mycobacterium wherein the mycobacterial cell entry gene is disabled, and immunogenic preparations including vaccines comprising the same.

SUMMARY OF INVENTION

The present invention provides attenuated strains of Mycobacteria which are useful in immunogenic compositions. In accordance with one aspect of the present invention, there is provided an attenuated strain of Mycobacterium wherein the mycobacterial cell entry (mce) gene is functionally disabled. By functionally disabling the mce gene, the ability of the Mycobacterium to invade and infect cells is removed. This attenuation permits the novel strains provided herein to be used in immunogenic compositions for administration to a host to generate an immune response.

The mce gene may be functionally disabled by an insertion into the gene such as to disrupt the mycobacterial cell entry function thereof. The mce gene also may be functionally disabled by deleting at least a part of the gene from the wild-type strain. In addition, mutagenesis of the mce gene may be used to attenuate the wild-type strain.

The mutant strain of Mycobacterium may be prepared by any convenient procedure. Homologous recombination conveniently may be used to replace the mce gene of the wild-type strain of Mycobacterium by a double cross-over event with a disabled mce gene.

The present invention is broadly applicable to strains of Mycobacterium, particularly a species of the tuberculosis complex, including *M. tuberculosis* and *M. bovis*.

In another aspect of the invention, there is provided a method of forming an attenuated strain of Mycobacterium, which comprises effecting allelic exchange of a mutant mycobacterial cell entry (mce) gene which is functionally disabled for a mycobacterial cell entry gene in a wild-type strain of Mycobacterium.

The mutant mce gene may contain a selectable marker, so that the attenuated strain of mycobacterium formed in the allelic exchange may be detected on the basis of the presence of the selectable marker therein.

A further aspect of the invention provides an immunogenic composition comprising the attenuated strain provided herein. Such immunogenic composition may be formulated as a vaccine for in vivo administration to a host to confer protection against disease caused by a virulent strain of Mycobacterium. The host may be a primate including a human.

The present invention includes, in a further aspect thereof, a method of generating an immune response in a host comprising administering thereto an immunoeffective amount of the immunogenic composition provided herein.

A yet further aspect of the invention provides a method of producing a vaccine for protection against a disease caused by infection by a virulent strain of Mycobacterium, which comprises administering the immunogenic composition provided herein to a first host to determine an amount and frequency of administration thereof to confer protection against the disease; and formulating the immunogenic composition in a form suitable for administration to a treated host in accordance with the determined amount and frequency of administration. The treated host may be a human.

The attenuated strains of Mycobacterium provided herein are useful as a live vaccine against diseases caused by Mycobacteria. Advantages of the present invention include the provision of safer and attenuated strains of Mycobacterium for the preparation of immunogenic compositions, including vaccines, and for the generation of immunological and diagnostic reagents.

BRIEF DESCRIPTION OF DRAWINGS

FIG. 1 illustrates the construction and restriction map of a disrupted mce gene. The hygromycin resistance gene (hyg) from *S. hygroscopicus* was inserted at the BsiWI site in the mce gene. Primers P4414 (SEQ ID NO: 1) and P4448 (SEQ ID NO: 2) are located respectively 5' and 3' of the BsiWI site. Only the 4.7 kb insert of plasmid pBCGcepX and the 6 kb insert of plasmid pBCGcepX-H are represented. The SacI site of plasmid pBlueScript SK+ from which these plasmids are derived is located in the multiple cloning site in 5' of the XhoI site. Digestion of plasmid pBCGcepX with SacI yields two bands (~3.75 kb and ~3.9 kb). Digestion of plasmid pBCGcepX-H with SacI yields three bands (~1.66 kb, ~3.45 kb and ~3.9 kb). The ApaI site of plasmid pBlueScript SK+ is located in the multiple cloning site in 3' of the XhoI site. Probe PMCE is represented by the bold arrow and covers the totality of the mce gene.

Lane 1: BCG wild-type)
Lane 2: BCG-65 (→digested by SacI
Lane 3: BCG-69 )
Lane 4: BCG wild-type)
Lane 5: BCG-65 (
Lane 6: BCG-69 )→digested by XhoI
Lane 7: BCG-73 (
Lane 8: BCG-83 )

For the XhoI digests, the wild-type strain gave a single band at 4.7 kb while the mutants gave a band at 6 kb, resulting from the presence of the hyg gene. BCG-69 gave two bands, confirming the presence of the wild-type copy of the gene as well as the disrupted one in the chromosome. While the wild-type mutant gave the 5.2 kb band for the SacI digest, the knock-out mutant, BCG-65, gave two bands at 4.8 kb and 1.7 kb resulting from the SacI site of the hyg gene integrated into the mice gene.

Lane 1: BCG-65
Lane 2: BCG-69
Lane 3: BCG wild-type

A monoclonal antibody against Mcep was used for the blotting. Mcep is not present in BCG-65, while produced by BCG-69 or BCG wild-type.

GENERAL DESCRIPTION OF THE INVENTION

The use of BCG. herein is a useful means of illustrating the broader application of the present invention to functionally disabling the mycobacterial cell entry gene in a strain of Mycobacterium, including any of the species of the tuberculosis complex, including *Mycobacterium tuberculosis*.

The provision of the strain of Mycobacterium in which the mce gene is functionally disabled provides attenuated strains of Mycobacterium which may be used safely in immunogenic compositions.

Figure 1:
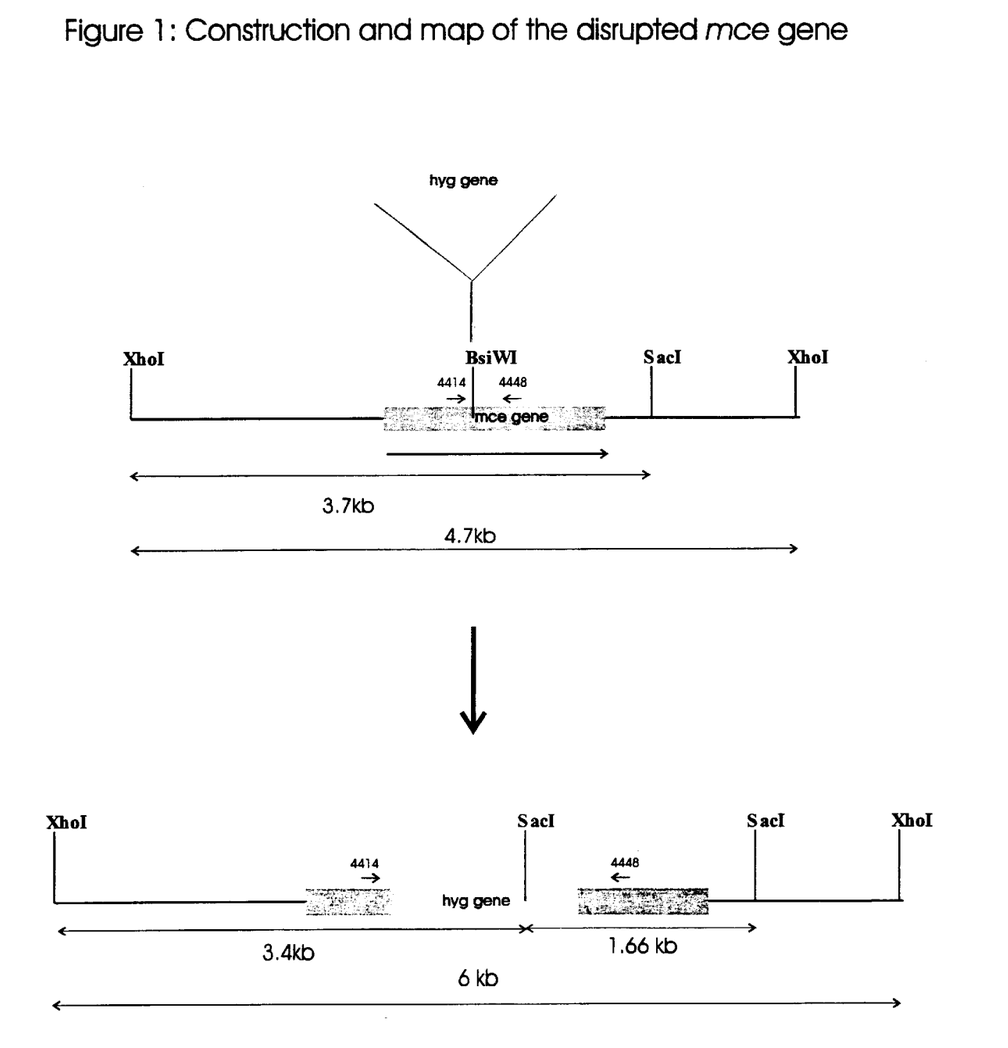

Referring to FIG. 1, there is illustrated therein the construction of a disrupted mce gene. Plasmid pBCGcepX, the preparation of which is described in the above mentioned U.S. application Ser. No. 08/677,970 and deposited under ATCC No. 97511, is digested with restriction enzyme BsiWI to cut the mce gene at the restriction site. In FIG. 1 only the 4.7 kb XhoI fragment of the plasmid is shown.

The hygromycin resistance gene (hyg) of *Streptomyces hygroscopices* is isolated from a plasmid pIDV6, obtained from ID Vaccines, by digestion with restriction enzyme NotI. Following separation of a 2.5 to 3 kb fragment, restriction enzyme BspHI is used to isolate a 1.3 kb fragment containing hyg gene.

The hyg gene is ligated with the BsiWI digested plasmid pBCGcepX and the ligate used to transform *E. coli*. Following selection for hygromycin resistance, transformants are grown and the plasmid isolated. Plasmid pBCGcepX-H, produced by this procedure, has the hyg gene inserted into the mce gene, in the opposite direction.

The plasmid BCGcepX-H is linearized and the linearized plasmid is used to transform a Mycobacterium strain, for example, *M. bovis* BCG, by homologous recombination. The construction by homologous recombination of mutants deficient in some metabolic genes has been achieved recently in slow growing mycobacteria (refs. 5, 6, 7). The suppression of key metabolic enzymes was expected to lead to the generation of less virulent strains, with little success so far (ref. 8).

Screening of recombinant events may be performed by PCR analysis. Hygromycin resistant *M. bovis* BCG colonies are subjected to PCR analysis using a pair of primers corresponding to appropriate portions of the mce gene. As seen in FIG. 1, primer P4414 (SEQ ID NO: 1) and P4448 (SEQ ID NO:2) (the nucleic acid sequences of the primers are shown in Table 1 below), are used for PCR amplification. Such primers generate a 572 bp PCR product for a wild-type strain while integration of the mutant, mce gene by homologous recombination with double cross-over yields a 1.9 kb product. For a random DNA integrate or a single cross-over, two fragments are amplified.

Figure 2:
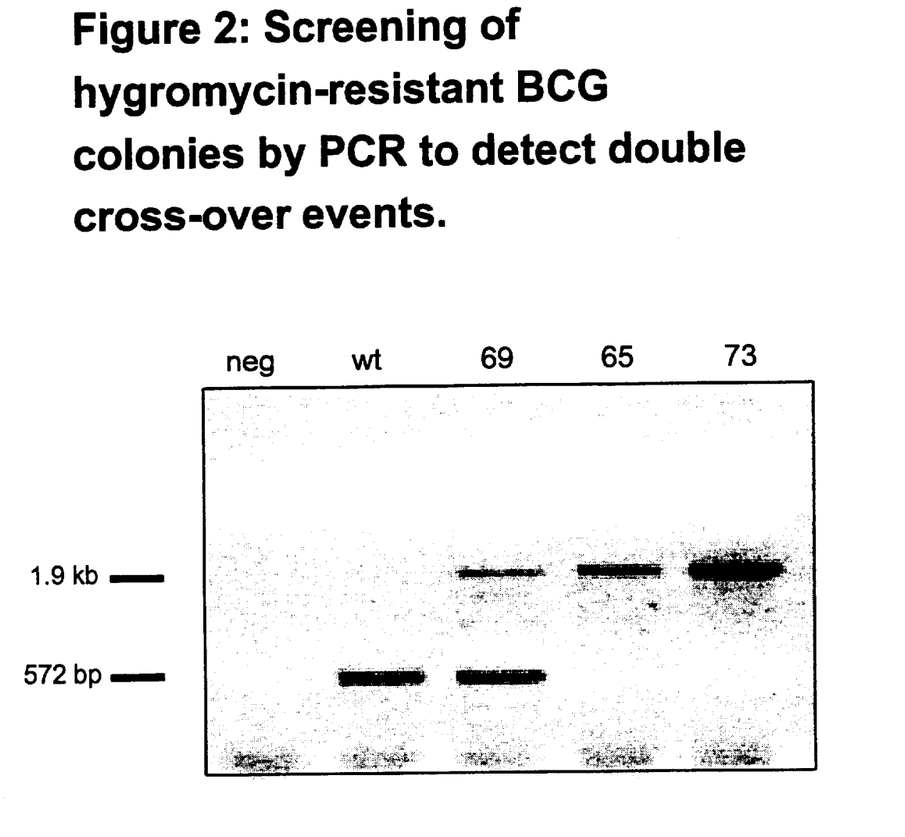
FIG. 2 contains a computer scan illustrating screening of hygromycin-resistant BCG colonies by PCR to detect double cross-over events in homologous recombination. The PCRs were performed on BCG colonies with primers P4414 and P4448. The expected amplification product is 572 bp for the wild-type (lane wt) and about 1.9 kb in case of a double cross-over event (lanes 65 and 73). In case of a single cross-over event or a non-specific integration, the presence of the two amplification products was expected. Lane neg: negative control, no DNA. Lane wt: BCG wild-type. A 572 bp fragment was amplified. Lane 69: BCG-69. Integration of plasmid pBCGcepX-H in the chromosome was the result of a single cross-over event, or a non-specific integration. The amplification reaction yields two products. Lane 65 and 73: BCG-65 and BCG-73. A double cross-over event lead to the integration of the mutated mce gene in the chromosome. A 1.9 kb fragment was amplified.

Three mutants (BCG-65, BCG-73, BCG-83) produced only a 1.9 kD PCR-amplified fragment, consistent with homologous recombination causing replacement of native mce gene by a disrupted copy of the gene. FIG. 2 shows the results of the PCR analysis. The wild-type strain produced a 572 bp fragment while a single cross-over mutant produced both fragments.

In order to further assess the recombinant BCG as to the proper integration of the functionally-disabled mce gene, a Southern blot was performed. This required isolating the chromosomal DNA from the recombinant BCG colonies and digesting them with restriction endonucleases, and transferring the DNA fragments separated on the agarose gel to a nylon membrane. The probe for the mce gene was PCR amplified from M. tuberculosis H37RV DNA as described in Example 6 below. The 1.6 kb probe was used to verify the double cross-over events that occurred in BCG-65, BCG-73 and BCG-83. These strains represent attenuated BCG containing the functionally disrupted mce gene.

Figure 4:
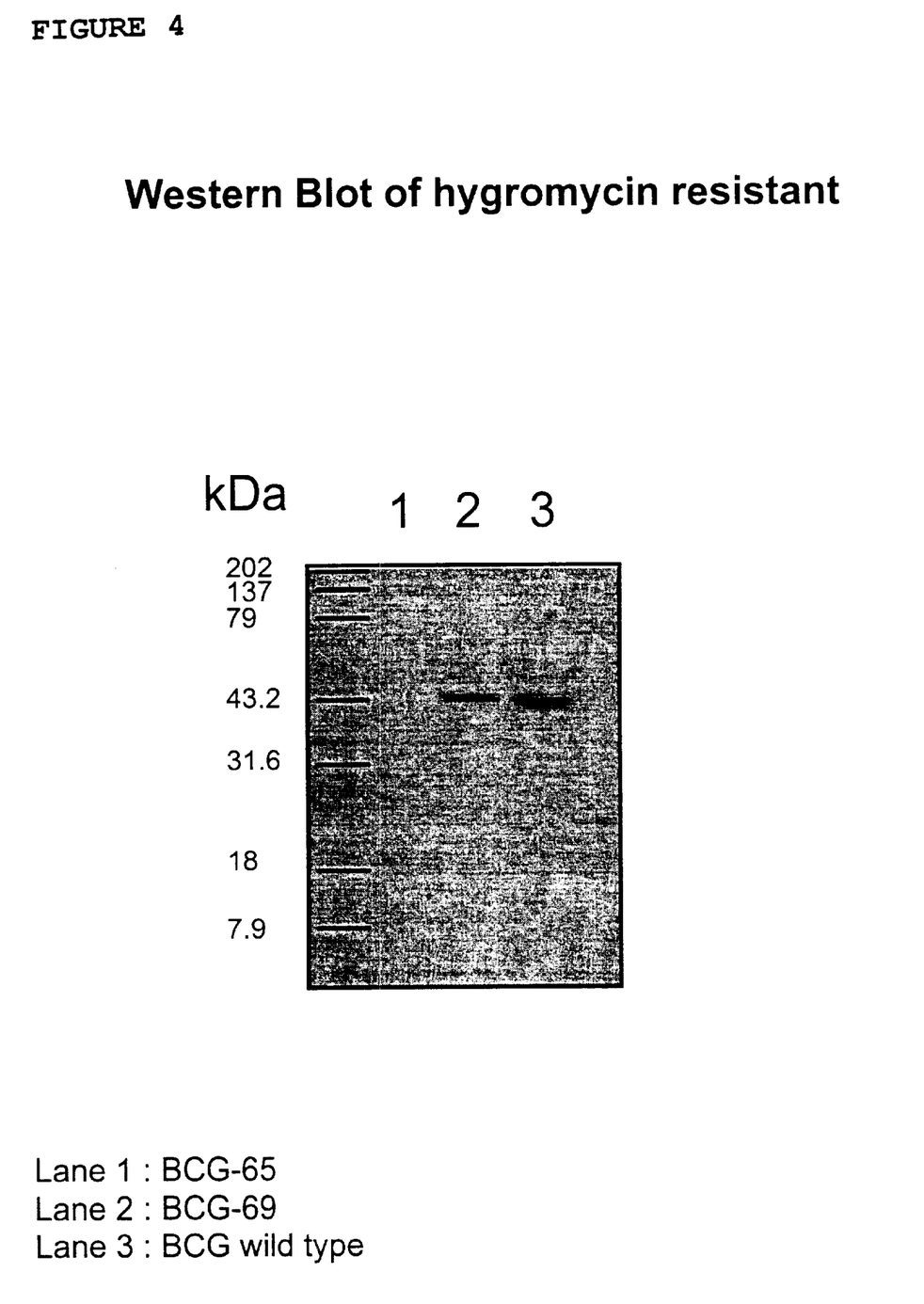
FIG. 4 contains a computer scan of a Western Blot analysis of Mcep produced by mutants.

To show that these attenuated BCG no longer produce the cell entry protein, Western blots were performed on cell lysates produced by sonication of the cells. A mycobacterial strain with a disrupted gene would not be able to make the Mce protein and, therefore, a mouse monoclonal antibody to the mycobacterial cell entry protein would not recognize any protein from this strain, as described in Example 7 below. FIG. 4, lane 1, clearly shows that such attenuated BCG, BCG-65, does not make any mycobacterial cell entry protein. A single cross-over or non-homologous recombinant, BCG-69, was not disrupted in the mce gene and still produced the wild-type mycobacterial cell entry protein (FIG. 4, lane 2).

Biological Deposits

A vector that contains the gene encoding a mycobacterial cell entry protein and having a molecular weight of between about 45,000 and about 60,000 from the *M. bovis* strain BCG that is described and referred to herein has been deposited with the American Type Culture Collection ,(.ATCC) located at 10801 University Boulevard, Manassas, Va. 20110-2209 USA, pursuant to the Budapest Treaty and prior to the filing of this application in connection with application Ser. No. 08/677,970 referred to above. Samples of the deposited vectors will become available to the public upon grant of a patent based upon this or the aforementioned U.S. patent application and all restrictions on access to the deposit will be removed at that time. Viable samples will be provided if the depository is unable to dispense the same. The invention described and claimed herein is not to be limited in scope by the biological material deposited, since the deposited embodiment is intended only as an illustration of the invention. Any equivalent or similar vectors that encode similar or equivalent antigens as described in this application are within the scope of the invention.

Deposit Summary

| Deposit | ATCC Designation | Date Deposited |
| --- | --- | --- |
| Plasmid pBCGcepX | 97511 | April 11, 1996 |

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

Example 1

This Example illustrates the recombinant DNA methods used herein.

Restriction enzymes and cloning vectors were obtained from several sources including New England Biolabs, Life Technologies, Boehringer Mannheim and Stratagene. The enzymes and buffers for the PCR were purchased from Perkin-Elmer or Sangon Corporation and used as per the manufacturers protocols.

Reagents used in DNA isolation protocols were purchased from Sigma Biochemicals. Most recombinant DNA manipulations were performed using standard protocols (ref. 10). Sequences of double stranded plasmid DNA were determined using the Taq Dye Deoxy Terminator cycle sequencing kit (Applied Biosystems) on a GeneAmp PCR system 9600 (Perkin-Elmer) and a run on a DNA analysis system, model 370A (Applied Biosystems) The sequence was assembled and processed using the IG software (IntelliGenetics Inc). The synthesis of oligonucleotides used as primers was performed using an Applied Biosystems (380B) synthetizer. The synthetic oligonucleotides were purified on OPC cartridges supplied by Applied Biosystems according to the manufacturers protocol. Example 2

This Example illustrates construction of the disrupted mce gene.

5 μg of plasmid pBCGcepX (ATCC # 97511) were digested with restriction enzyme BsiWI (NEB Biolabs) for 2 hours at 37° C. in 25 μl final volume. 3 μl of Nick translation buffer, 1 μ of dNTP's (2mM) and 2 units of Klenow DNA Polymerase (Boehringer Mannheim) were added to the solution and it was incubated for 30 min at room temperature. 120 μl of water were added and a phenol-chloroform extraction was performed by mixing: 75 μl of phenol (Life Technologies) and 75 μl of chloroform-isoamyl acid (24: 1, v:v) to the solution. The tube was spun (12000 xg for 2 min) and the aqueous phase was transferred to a fresh tube. 300 μl of ice-cold 100% ethanol was added, the DNA was pelleted by centrifugation (12000 g for 15 min at 4° C.), and washed with 1 ml of 70% ethanol. The DNA was air dried at room temperature and resuspended in 40 μl of water. 3 units of Calf Intestinal Alkaline Phosphatase (Boehringer Mannheim) were added and the mixture was incubated at 37° C. for 1 hour in 50 μl volume final. The DNA was purified from an agarose gel, and resuspended in 30 μl of water.

To isolate the hygromycin resistance gene (hyg) of *Streptomyces hygroscopicus*, 18 μg of plasmid pIDV6 (obtained from Dr Horwitz, University of California, Los Angeles, Calif.) were digested with the restriction enzyme NotI (NEB Biolabs) for 3 hours at 37° C. in 60 μl volume final. The digestion of plasmid pIDV6 with NotI resulted in two products, namely a 2.5 to 3 kb fragment containing the hyg gene and a larger fragment. The 2.5 kb band was purified and resuspended in 20 μl of water. The restriction enzyme BspHI (NEB Biolabs) was added to the DNA and the mixture was incubated at 37° C. for 2 hours 30 min, in 30 μl final volume. 3,5 μl of Nick translation buffer, 1 μl of dNTP's (2mM) and 2 units of Klenow DNA Polymerase (Bochringer Mannheim) were added to the solution and the mixture was incubated for 30 min at room temperature. The digest was run on a 0,8% agarose gel, and consisted in two products, namely a 1.3 kb fragment and a smaller one. The larger piece of DNA, containing the hyg gene, was purified from the gel and resuspended in 15 μl of water.

The ligation was performed in a final volume of 20 μl, using 1 μl of plasmid pBCGcepX digested by BsiWI and treated as described above and 4 μl of the hyg gene isolated as described above. 1.5 units of T4 DNA Ligase (Life Technologies) were used in this reaction. The mixture was incubated overnight at 16° C. to ligate the hyg gene with the digested pBCGcepX plasmid.

2 μl of the ligation mixture were used to transform 70 μl of electro-competent *E. coli* HB101 cells, and 100 μl of the transformation solution were plated onto Luria-Bertani agar (LB agar), with 100 μg/ml of ampicillin and 200 μg/ml of hygromycin B (Boehringer Mannheim). A few transformants were isolated and grown up. The plasmids were isolated using a kit for high grade plasmid purification (Qiagen) and sequenced. One of them, plasmid pBCGcepX-H, had the hyg gene inserted in the mce gene, in the opposite direction (see FIG. 1). 50 μg of plasmid pBCGcepX-H were digested with the restriction enzyme Apal (Life Technologies) for 3 hours at 30° C. in 200 μl final volume. After incubation, 100 μl of water were added and the DNA was purified by phenol extraction, followed by two phenol-chloroform extractions. The aqueous solution was transferred to a new tube, 35 μl of 3M sodium acetate were added, the DNA was precipitated by adding 1 ml of ice-cold 100% ethanol. The DNA was pelleted by centrifugation (12000 g for 10 min at 4° C.), washed with 70% ethanol, air dried and resuspended in 25 μl of water. The concentration of DNA was determined by reading the OD at 260 nm. Example 3

This Example illustrates transformation of *M. bovis* BCG with plasmid pBCGcepX-H Electrocompetent *M. bovis* BCG cells were prepared using a modification of a protocol already described (ref. 9). 500 μl of a frozen stock of Connaught *M. bovis* BCG strain were used to inoculate 10 ml of 7H9-ADC-Tw broth and incubated with shaking at 37° C. for three days. Two ml of this preculture were used to inoculate 100 ml of 7H9-ADC-Tw broth and incubated at 37° C. with shaking for three days. 1.5 g of glycine (Boehringer Mannheim) diluted in 10 ml of water and sterile-filtered was added to the culture and the culture was incubated one more day.

The electrocompetent cells were spun down (4000 μg for 15 min) and sequentially washed in 100, 50, 25, 10 ml of 10% glycerol. The cells were eventually E resuspended in 3 ml of 10% glycerol.

A 0.25 ml aliquot of resuspended cells was mixed with 3 μg of linearized plasmid pBCGcepX-H, the mixture was incubated on ice for 10 min and subjected to electroporation in a 0.2 cm cuvette using a BioRad apparatus (BioRad,) at a setting of 2,5 kV, capacitance of 25 μF. and pulse controller to 1000 Ω. The cells were then placed on ice for 10 min, resuspended in 1 μl ADC-TW broth and incubated for 3 hours with shaking at 37° C. The transformed cultures were spread on 7H10 agar plates containing 50 μg/ml of hygromycin B and 100 μg/ml of cycloheximide(Sigma) and incubated at 37° C. for 3 to 4 weeks. Example 4

This Example illustrates PCR amplification of the *M. bovis* BCG colonies.

Screening of recombinant events was performed by PCR reactions. Hygromycin-resistant *M. bovis* BCG colonies, prepared as described in Example 3, were isolated, used to inoculate 3 ml of 7H9-ADC-Tw broth, and incubated for three days at 37° C. 1 ml of this culture was transferred to a microfuge tube, and spun down (12000 g for 10 min) to pellet the cells. The cells were resuspended in 50 μl of water, boiled for 10 min and immediately placed on ice. The amplification reactions were carried out using the "Hot Start" procedure. Essentially, a 40 μl reaction mix containing dNTP's (0.2 mM in 100 μl final volume), buffer and a pair of primers (P4414, SEQ ID NO:1, and P4448, SEQ ID NO:2; 100 pM of each, see Table 1 below for identification of the primers) was prepared in thin-wall Eppendorf tubes. To each tube, a bead of wax (PCRGem 100, Perkin-Elmer) was added and the tube was heated to 70° C. for 5 min. Subsequently, the tube was cooled at room temperature for 5 min and a reaction mix (60 μl) containing buffer, 1 unit of enzyme and 25 μl of the colony preparation was added. The tubes were then placed in a Perkin-Elmer Cetus thermal cycler and a cycling sequence started based on the following parameters:

Step 1: 2 min at 99° C.;

Step 2: 45 sec at 98° C.; 45 sec at 60° C.; 1 min 30 sec at 72° C.; repeated for 25 cycles;

Step 3: 10 min at 72° C.;

Step 4: maintain at 4° C.

The tubes were stored at 4° C.; aliquots of 10 μl were run on a 0,8% agarose gel and the electrophoretic patterns visualized and photographed.

The set of primers used generated a 572 bp PCR product for wild type BCG strain, while integration by homologous recombination with double cross-over yielded a 1.9 kb product. If the DNA integrated randomly or by a single cross-over, then two fragments were amplified. Analysis of 88 transformants by PCR analysis showed three mutants (BCG-65, -73, -83) yielding only a 1.9 kb fragment, as expected from homologous recombination causing replacement of the native mce gene by a disrupted copy of the gene. The 1.9 kb and 572 bp fragments were amplified for all the other transformants.

FIG. 2 shows the results of the PCR screening described above. As may be seen therein, the mutant strain wherein a double cross-over event has caused replacement of the native mce gene by a disrupted form of the gene contained a 1.9 kb fragement (lanes 65, 73). The wild-type strain contained the 572 bp fragment (lane wt) while a random-integrate or a single cross-over mutant contained both the 572 bp fragment and the 1.9 kb fragment (lane 69).

Example 5

This Example illustrates the preparation of genomic DNA from *M. bovis* BCG

Genomic DNA from BCG cultures was extracted using a modification of a technique already described (ref. 11). 50 ml of a 14 days BCG culture was centrifuged (6000 μg for 10 min) to pellet the cells. The pellet was incubated for one hour at 370° C. in 1 ml of TE buffer (10 mM Tris-HC1, pH7.5 and lmM EDTA) containing 200 μg/ml of proteinase K (Life Technologies) and 10 μg/ml of hen egg-white lysozyme (Sigma, St Louis, Mo., USA). After centrifugation (12000 g for 5 min), the pellet was resuspended in 1 ml of DNAzol (Life Technologies), transferred to a 2 ml screw-capped tube filled to a quarter with glass beads (106 μm or finer, Sigma) and vortexed vigourously for 10 min. The beads were allowed to settle and the supernatant was transferred to a fresh tube and centrifuged for 10 min at room temperature. The resultant lysate was transferred to a new tube and the DNA was precipitated by adding 0.5 ml of 100% ethanol. The tube was inverted several times to mix the materials and the mixture was incubated at room temperature for 3 to 5 min. The tube was spun (at 1000 g for 2 min) to pellet the DNA, the supernatant discarded, the pellet washed twice with 1 ml of 95% ethanol, air-dried at room temperature and resuspended in 200 μl of TE buffer. The quantity of DNA was estimated by measuring the optical density (OD) at 260 nm in a spectrophotometer. This protocol yielded approximately 80 μg of DNA. Example 6

This Example illustrates the preparation of the DIG-labelled mce probe and Southern hybridization of BCG DNA digests.

PCR reactions were carried out on 500 ng of *M. tuberculosis* H37Rv DNA, using primers P4973 (SEQ ID NO:3) and P4974 (SEQ ID NO:4), located at the extremities of the mce gene of *M. bovis* BCG. PCR reactions were carried out as described in Example 4, except that the template was 500 ng of *M. tuberculosis* H37Rv DNA instead of 25 μl of a colony DNA preparation. The amplification product (1.6 kb) was isolated by excising the band from a 0.8% agarose gel and extracting the DNA. The isolated DNA was labelled with DIG-dUTP, using the DIG-labelling kit (Boehringer-Mannheim), following the supplier's instructions. This procedure yielded the probe identified herein as PMCE. The sequence of the mce gene of *M. tuberculosis* H37Rv is 99% identical to the mce gene of *M. bovis* BCG.

8 μg of BCG DNA was digested in a 40 μl final volume, for 3 hours at 37° C., with SacI or XhoI restrictions enzymes. The digests were run out on a 0.8% agarose gel. The gel was transferred to a nylon membrane (GeneScreen Plus, Dupont) using standard reagents and protocols and the DNA fixed to the membrane.

The membrane was prehybridized, hybridized overnight at 65° C. with the labelled probe PMCE and subsequently washed. The membrane was processed following the instructions of the kit supplier (Boehringer Mannheim). The blot was exposed to a film for 3 min at room temperature and the radiograph developed (see FIG. 3).

Figure 3:
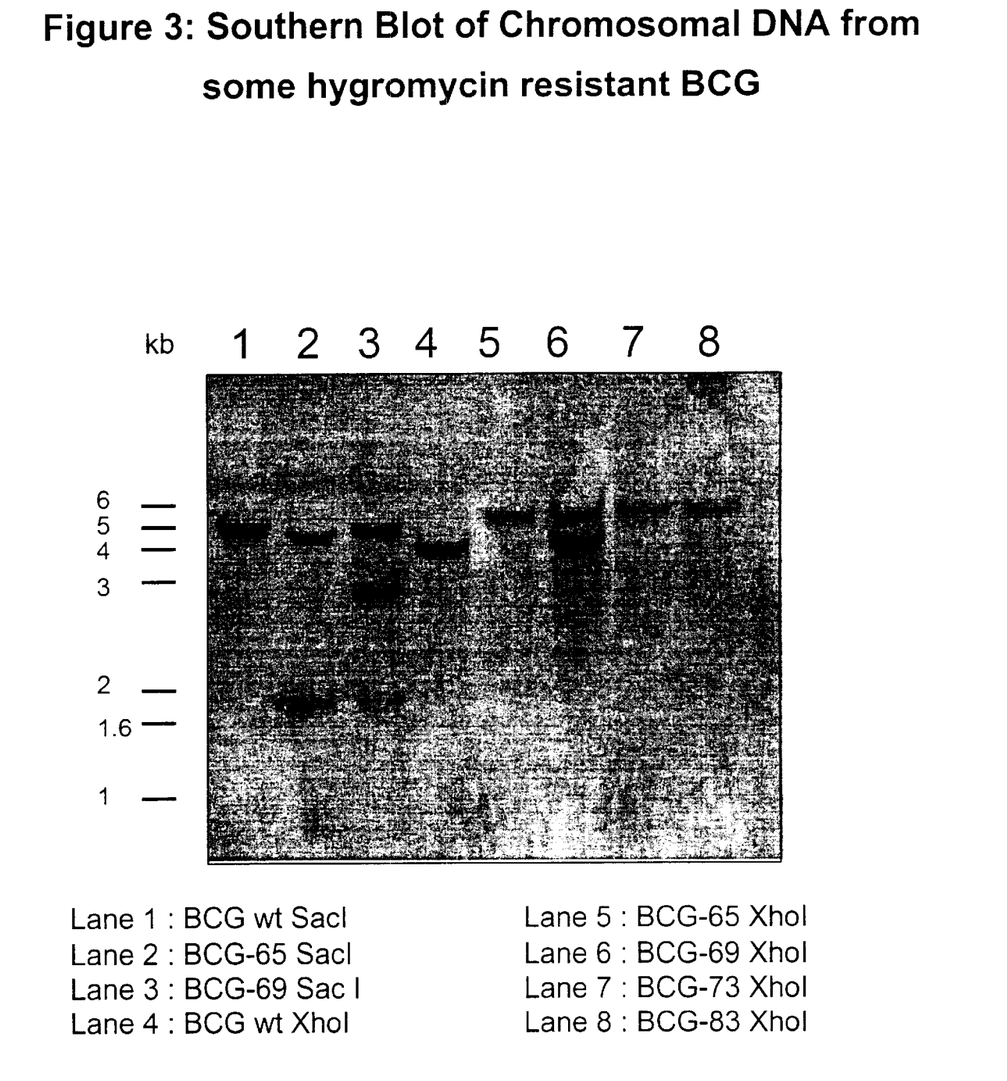
FIG. 3 contains a computer scan of a Southern Blot analysis of chromosomal DNA from BCG strains.

FIG. 3 shows the results of the Southern Blot analysis performed as described above. Lanes 1 to 3 show the results for the SacI digests. The wild-type strain (Lane 1) gave a single band as 5.2 kb while the knock-out mutant BCG-65 (Lane 2) gave two bands at 4.8 kb and 1.7 kb resulting from the SacI site of the hyg gene integrated into the mce gene. The single cross-over mutant BCG-69 (Lane 3) gave three bands.

Lanes 4 to 8 show the results of the XhoI digests. The wild-type strain (Lane 4) gave a single band at 4.7 kb while the knock-out mutants BCG-65 (Lane 5), BCG-73 (Lane 7) and BCG-83 (Lane 8) gave a single band at 6 kb resulting from the presence of the hyg gene. The single cross-over mutant BCG-69 (Lane 6) gave two bands.

Example 7

This Example illustrates Western Blot analysis of the BCG transformants.

*M. bovis* BCG transformants, prepared as described in Example 3, were grown in 10 ml of 7H9-ADC-Tw with 50 μg/ml of hygromycin, to an optical density at 600 nm of 2. 1.5 ml of the culture was harvested, spun down (12000×g for 10 min) and transformants resuspended in 200 μl of water. The solution was submitted to two 30 sec sonication cycles in a Sonifer 250 sonicator (Branson) at full power. The lysate was mixed with 4×UMS buffer (0.1 M Tris-HCL, pH8; 20% glycerol; 8% SDS; 48% urea, 8% β-mercaptoethanol; trace of bromophenol blue). 8 μl of the mixture was boiled for 10 min, resolved on a 12.5% acrylamide gel and transferred to a polyvinylidene fluoride membrane (Immobilon-P, Millipore). The membrane was processed using the Western Blotting system from Boehringer Mannheim, following the manufacturer's instructions. Mouse monoclonal antibodies against the mycobacterial cell entry protein (Mcep) were used for the blotting at a concentration of 1 μg/ml. The anti-mouse horseraddish peroxydase-conjugated secondary antibody (Bochringer Mannheim) was used according to the supplier's recommendations. The blot was exposed to a film for 5 min at room temperature and the auto radiograph developed (see FIG. 4).

FIG. 4 shows the Western Blot results. The monoclonal antibody to Mcep detected no production of Mcep by the knock-out mutant BCG-65 (Lane 1) while production of Mcep by both the single cross-over mutant BCG-69 (Lane 2) and wild-type (Lane 3) was detected.

SUMMARY OF THE DISCLOSURE

In summary of this disclosure, the present invention provides mutants of Mycobacterium strains in which the expression of the mycobacterial cell entry protein is disabled. Modifications are possible within the scope of the invention.

TABLE 1

Sequence of PCR Primers

| PRIMER # | SEQUENCE (5'–3') | SEQ ID NO |
|---|---|---|
| p4414 | GTATGTGTCGTTGACCACGCC | 1 |
| P4448 | TCAGGTCGATCGGCATCGTAGAAG | 2 |
| P4973 | TTTCAAACGTTCCTGCGTCCC | 3 |
| P4974 | CGAGTTTGACGATTCCAG | 4 |

REFERENCES

1. Grange, J. M.; Gibson J; Osborn, T. W.; Collins, C. H. and Yates, M. D. (1983), Tubercle 64: 129–139.
2. PCT; WO 95/17511, Jacobs, W. R. Jr.; Bloom B .R., Collins, D. M., Delisle, G. W.; Pascopella, L. and Kawakami R. P.
3. Shepard, C. C. (1958), J. Exp. Med. 107: 237–45.
4. Arruda, S., Bonfim, G.; Huma-Byron, T. and Riley L.W. (1993), Science 261: 1454–1457.
5. Azad, A. K., Sirakova T. D., Rogers L. M., Kolttukudy P. E. (1996) PNAS 93: 4787–4792.
6. Balasubramanicm V.M. et al (1996) J. Bacteriol 178:273–279.
7. Reyrat J. M., Berthet F. X., Gicquel B. (1995) PNAS 92:8768–8772.
8. Reyrat J. M, Lopez-Ramirez G, Ofredo C, Gicquel B, Winter N. (1996), Urease activity does not contribute dramatically to persistence of Mycobacterium bovis bacillus Calmette-Guerin. Infect. Immun. 64.pp 3934–3936.
9. Jacobs Jr W. R., Kalpana G. V., Cirillo J. D., Pascopella L, Snapper S B., Udani R A., Jones W., Barletta R G., Bloom B R. (1991) Genetic systems for Mycobacteria. Methods Enzymol. 204 pp 537–555.
10. "Molecular Cloning: A Laboratory Manual", ed Sambrook. J.; Fritsch, E. F. and Maniatis, T. (1989) Cold Spring Harbour Laboratory Press.
11. Anderberg, R. J., Strachan, J. A. and Cangelosis, G. A. (1995) Bio Techniques 18:217–219.

What we claim is:

1. A method of forming a strain of Mycobacterium which is a species of the tuberculosis complex, which comprises:

effecting allelic exchange of a mutant mycobacterial cell entry (mce) gene which is functionally disabled for a mycobacterial cell entry gene in a wild-type strain of Mycobacterium which is a species of the tuberculosis complex.

2. The method of claim 1 wherein said mutant mce gene contains a selectable marker and strains of said Mycobacterium formed in said allelic exchange are detected on the basis of the presence of the selectable marker therein.

3. The method of claim 1 wherein said wild-type strain of Mycobacterium is a strain of *Mycobacterium tuberculosis*.

4. The method of claim 1 wherein said wild-type strain of Mycobacterium is a strain of *Mycobacterium bovis*.

* * * * *